US00PP24816P2

(12) United States Plant Patent
Luo

(10) Patent No.: US PP24,816 P2
(45) Date of Patent: Aug. 26, 2014

(54) ***MANDEVILLA* PLANT NAMED 'ALEGNUFLOR999'**

(50) Latin Name: *Mandevilla hybrida*
Varietal Denomination: Alegnuflor999

(75) Inventor: Shuming Luo, Dulwich Hill (AU)

(73) Assignee: Nuflora International Pty. Ltd., Macquarie Fields, NSW (AU)

( * ) Notice: Subject to any disclaimer, the term of this patent is extended or adjusted under 35 U.S.C. 154(b) by 137 days.

(21) Appl. No.: 13/573,163

(22) Filed: Aug. 27, 2012

(51) Int. Cl.
*A01H 5/00* (2006.01)

(52) U.S. Cl.
USPC ..... Plt./232

(58) Field of Classification Search
USPC ..... Plt./232
See application file for complete search history.

(56) References Cited

U.S. PATENT DOCUMENTS

PP11,556 P * 10/2000 Tachibana et al. ..... Plt./232

OTHER PUBLICATIONS

UPOV PLUTO Citation for 'Alegnuflor999' Feb. 2013.*

* cited by examiner

*Primary Examiner* — Wendy C Haas
(74) *Attorney, Agent, or Firm* — C. A. Whealy

(57) ABSTRACT

A new and distinct cultivar of *Mandevilla* plant named 'Alegnuflor999', characterized by its upright and vining to climbing plant habit; vigorous growth habit; early and freely flowering habit; long flowering period; light pink-colored flower buds and developing flowers; relatively large white-colored flowers; and good garden performance.

2 Drawing Sheets

Botanical designation: *Mandevilla hybrida.*
Cultivar denomination: 'ALEGNUFLOR999'.

BACKGROUND OF THE INVENTION

The present invention relates to a new and distinct cultivar of *Mandevilla* plant, botanically known as *Mandevilla hybrida* and hereinafter referred to by the name 'Alegnuflor999'.

The new *Mandevilla* plant is a product of a planned breeding program conducted by the Inventor in Cobbitty, New South Wales, Australia. The objective of the breeding program is to create new *Mandevilla* plants that flower for a long period of time and have glabrous elliptic leaves and large white-colored flowers.

The new *Mandevilla* plant originated from a cross-pollination made by the Inventor in Cobbitty, New South Wales, Australia in October, 2008 of a proprietary selection of *Mandevilla hybrida* identified as code number X07.1.1, not patented, as the female, or seed parent with a proprietary selection of *Mandevilla hybrida* identified as code number X07.1.3, not patented, as the male, or pollen, parent. The new *Mandevilla* plant was discovered and selected by the Inventor as a single flowering plant from within the progeny of the stated cross-pollination in a controlled greenhouse environment in Cobbitty, New South Wales, Australia in December, 2009.

Asexual reproduction of the new *Mandevilla* plant by cuttings in Macquarie Fields, New South Wales, Australia since January, 2010 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of 'Alegnuflor999'. These characteristics in combination distinguish 'Alegnuflor999' as a new and distinct *Mandevilla* plant:

1. Upright and vining to climbing plant habit.
2. Vigorous growth habit.
3. Early and freely flowering habit.
4. Long flowering period.
5. Light pink-colored flower buds and developing flowers.
6. Relatively large white-colored flowers.
7. Good garden performance.

Plants of the new *Mandevilla* can be compared to plants of the female parent selection. Plants of the new *Mandevilla* differ primarily from plants of the female parent selection in the following characteristics:

1. Lower surfaces of leaves of plants of the new *Mandevilla* are smooth whereas lower surfaces of leaves of the female parent selection are coarse.
2. Plants of the new *Mandevilla* and the female parent selection differ in flower color as plants of the female parent selection have pink-colored flowers.

Plants of the new *Mandevilla* can be compared to plants of the male parent selection. Plants of the new *Mandevilla* differ primarily from plants of the male parent selection in flower color as plants of the male parent selection have pink-colored flowers.

Plants of the new *Mandevilla* can be compared to plants of *Mandevilla boliviensis* 'Sunmandeho', disclosed in U.S. Plant Pat. No. 11,556. In side-by-side comparisons conducted in Cobbitty, New South Wales, Australia, plants of the new *Mandevilla* differed primarily from plants of 'Sunmandeho' in the following characteristics:

1. Plants of the new *Mandevilla* had shorter leaves than plants of 'Sunmandeho'.
2. Plants of the new *Mandevilla* had smaller flowers than plants of 'Sunmandeho'.
3. Flower petals of plants of the new *Mandevilla* were not imbricate whereas flower petals of plants of 'Sunmandeho' were imbricate.
4. Plants of the new *Mandevilla* and 'Sunmandeho' differed in flower color as plants of 'Sunmandeho' had yellowish white-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the following detailed botanical description which accurately describe the actual colors of the new *Mandevilla* plant.

The photograph on the first sheet comprises a side perspective view of a typical flowering plant of 'Alegnuflor999' grown in a container.

The photograph on the second sheet are close-up views of flower buds, developing flowers and upper and lower surfaces of fully opened flowers of 'Alegnuflor999'.

DETAILED BOTANICAL DESCRIPTION

The aforementioned photographs and following observations, measurements and values describe plants grown in 45-cm containers during the autumn in a shaded outdoor nursery in Cobbitty, New South Wales, Australia and under cultural practices typical of commercial *Mandevilla* production. During the production of the plants, day temperatures ranged from 15° C. to 25° C., night temperatures ranged from 10° C. to 14° C. and light levels ranged from 2,500 to 3,000 foot candles. Plants were 30 months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Alegnuflor999'.

Parentage:

*Female, or seed, parent*.—Proprietary selection of *Mandevilla hybrida* identified as code number X07.1.1, not patented.

*Male, or pollen, parent*.—Proprietary selection of *Mandevilla hybrida* identified as code number X07.1.3, not patented.

Propagation:

*Type*.—By cuttings.

*Time to initiate roots, summer*.—About ten days at 25° C. to 30° C.

*Time to initiate roots, winter*.—About 16 days at 15° C. to 20° C.

*Time to produce a rooted young plant, summer*.—About four weeks at 25° C. to 30° C.

*Time to produce a rooted young plant, winter*.—About six weeks at 15° C. to 20° C.

*Root description*.—Medium in thickness, fleshy; white in color becoming creamy to golden brown with development.

*Rooting habit*.—Freely branching; dense.

Plant description:

*Plant and growth habit*.—Upright and vining to climbing plant habit; vigorous growth habit; moderate to rapid growth rate.

*Plant height*.—About 150 cm.

*Plant diameter*.—About 60 cm.

*Lateral branch description*.—Branching habit: Moderate to low branching habit; pinching enhances lateral branch development. Young branches: Diameter: About 2 mm to 3 mm. Internode length: About 20 cm. Texture: Smooth, glabrous. Color, shaded: Close to 144A; at leaf nodes, close to 185B; under full sunlight conditions, color becomes closer to 199A. Color, full sunlight: Close to 199A; at leaf nodes, close to 185B. Developing branches: Diameter: About 3.5 mm to 5 mm. Internode length: About 30 cm. Texture: Smooth, glabrous. Color: Close to 144A to 144B; under full sunlight conditions, color becomes closer to 199A. Mature branches: Diameter: About 9 mm to 10 mm. Internode length, distally: About 24 cm. Internode length, towards the base of the plant: About 6 cm. Texture: Smooth, glabrous. Color: Close to 144B; under full sunlight conditions, color becomes closer to 199D.

Foliage description:

*Arrangement*.—Opposite, simple.

*Length*.—About 10 cm.

*Width*.—About 5.5 cm.

*Shape*.—Elliptic.

*Apex*.—Acuminate.

*Base*.—Subcordate to obtuse.

*Margin*.—Entire; slightly undulate.

*Texture, upper and lower surfaces*.—Smooth, glabrous; leathery.

*Venation pattern*.—Pinnate, arcuate.

*Color*.—Developing leaves, upper surface: Close to 144A; occasionally, margins and midrib tinted with close to 185B. Developing leaves, lower surface: Close to 146D. Fully expanded leaves, upper surface: Close to N137A; venation, close to N144A to N144B. Fully expanded leaves, lower surface: Close to 146C; venation, close to 144B.

*Petioles*.—Length: About 2 cm to 2.5 cm. Diameter: About 2 mm to 3 mm. Texture, upper and lower surfaces: Smooth, glabrous. Color, developing leaves, upper and lower surfaces: Close to 144A; towards the base, moderately tinted with close to 185B. Color, fully expanded leaves, upper and lower surfaces: Close to 144B.

Flower description:

*Flower type and habit*.—Salverform flowers arranged alternately in terminal and axillary clusters; flowers face horizontally to slightly upright; freely flowering habit, about seven to ten flowers and flower buds per cluster.

*Natural flowering season*.—Early flowering habit and long flowering period, plants flower continuously year-round in the greenhouse and in an outdoor nursery from spring to autumn in New South Wales, Australia.

*Flower longevity on the plant*.—About three to four days; flowers not persistent.

*Fragrance*.—Very slightly fragrant, pleasant.

*Flowers*.—Appearance: Funnelform with five-parted fused corolla; flowers roughly star-shaped. Diameter: About 7.5 cm to 10 cm. Depth (length): About 7.5 cm to 8.5 cm. Throat diameter: About 1.5 cm to 1.9 cm. Tube length: About 7.5 cm to 8.5 cm.

*Flower buds*.—Height: About 7 cm. Diameter: About 1.2 cm. Shape: Elongated oblong. Color: Close to 157A tinged with close to 185D.

*Corolla*.—Arrangement and appearance: Single whorl of five petals, petals not imbricate. Petal lobe length: About 3.5 cm to 4 cm. Petal lobe width: About 3 cm. Petal lobe shape: Roughly orbicular. Petal apex: Rounded to occasionally cuspidate. Petal margin: Entire; slightly to moderately undulate and reflexing. Petal texture, upper and lower surfaces: Smooth, glabrous; velvety. Throat texture: Smooth, glabrous. Tube texture: Smooth, glabrous. Color, when opening: Petal lobe, upper and lower surfaces: Close to 65B. Throat: Close to 13B. Tube: Close to 65B. Color, fully opened: Petal lobe, upper and lower surfaces: Close to NN155C. Throat: Close to 17B to 17C. Tube: Close to 158D.

*Sepals*.—Arrangement and appearance: Five per flower fused in a single whorl. Length: About 5 mm. Width: About 3.5 mm. Shape: Lanceolate. Apex: Acute. Margin: Entire. Texture, upper and lower surfaces: Smooth, glabrous. Color, upper and lower surfaces: Close to 144A tinted with close to 185C.

*Pedicels*.—Length: About 1.5 cm. Diameter: About 2 mm. Texture: Smooth, glabrous. Strength: Strong, flexible. Color: Close to 144B.

*Reproductive organs*.—Stamens: Quantity per flower: Typically five. Filament color: White. Anther shape: Narrowly oblong. Anther color: White. Pollen amount: None observed. Pistils: Quantity per flower: Typically one. Stigma shape: Rounded; five-lobed. Stigma color: Light green. Style color: Light green. Ovary color: Light green.

*Seeds and fruits*.—Seed and fruit production has not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to have good garden performance and to tolerate rain, wind, full sunlight and temperatures from about 5° C. to about 45° C.

It is claimed:

1. A new and distinct *Mandevilla* plant named 'Alegnuflor999' as illustrated and described.

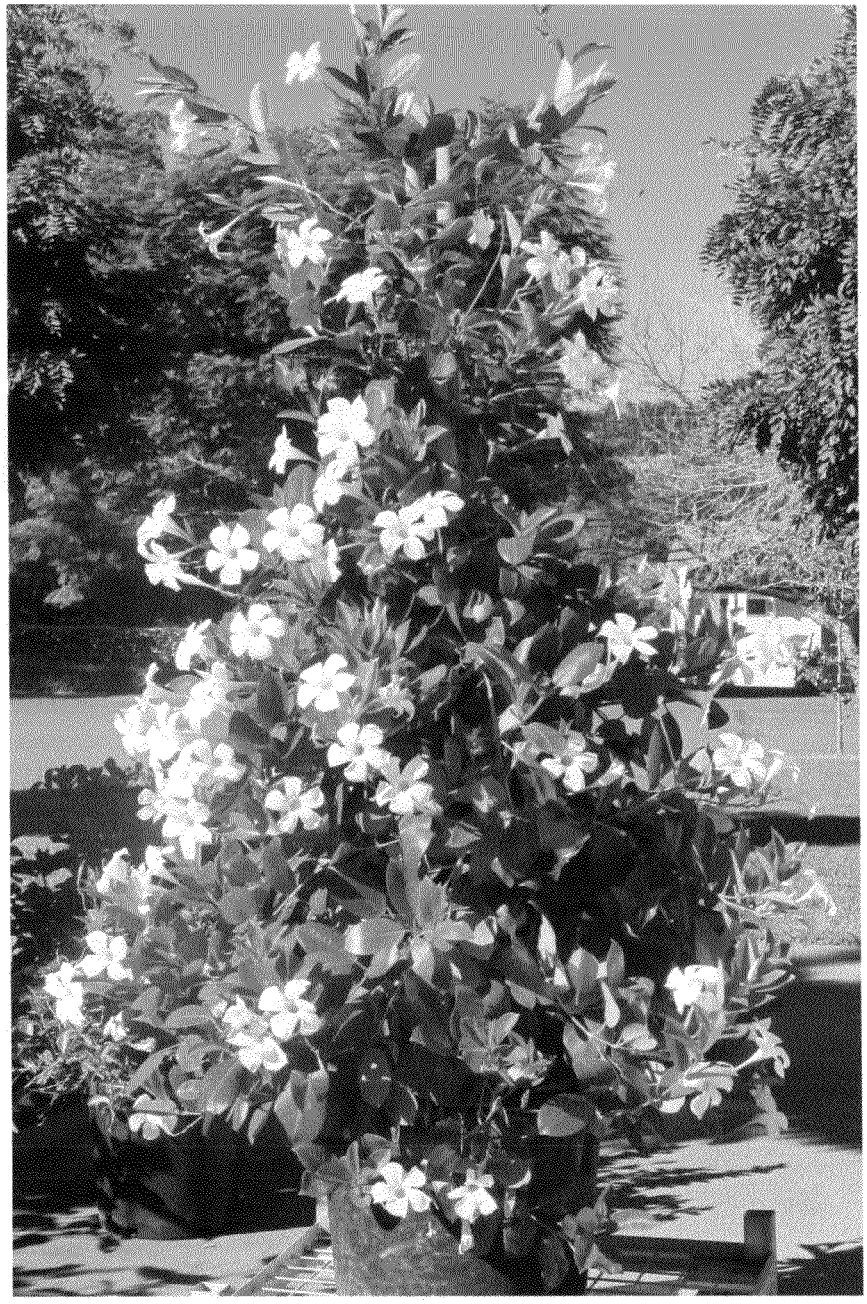

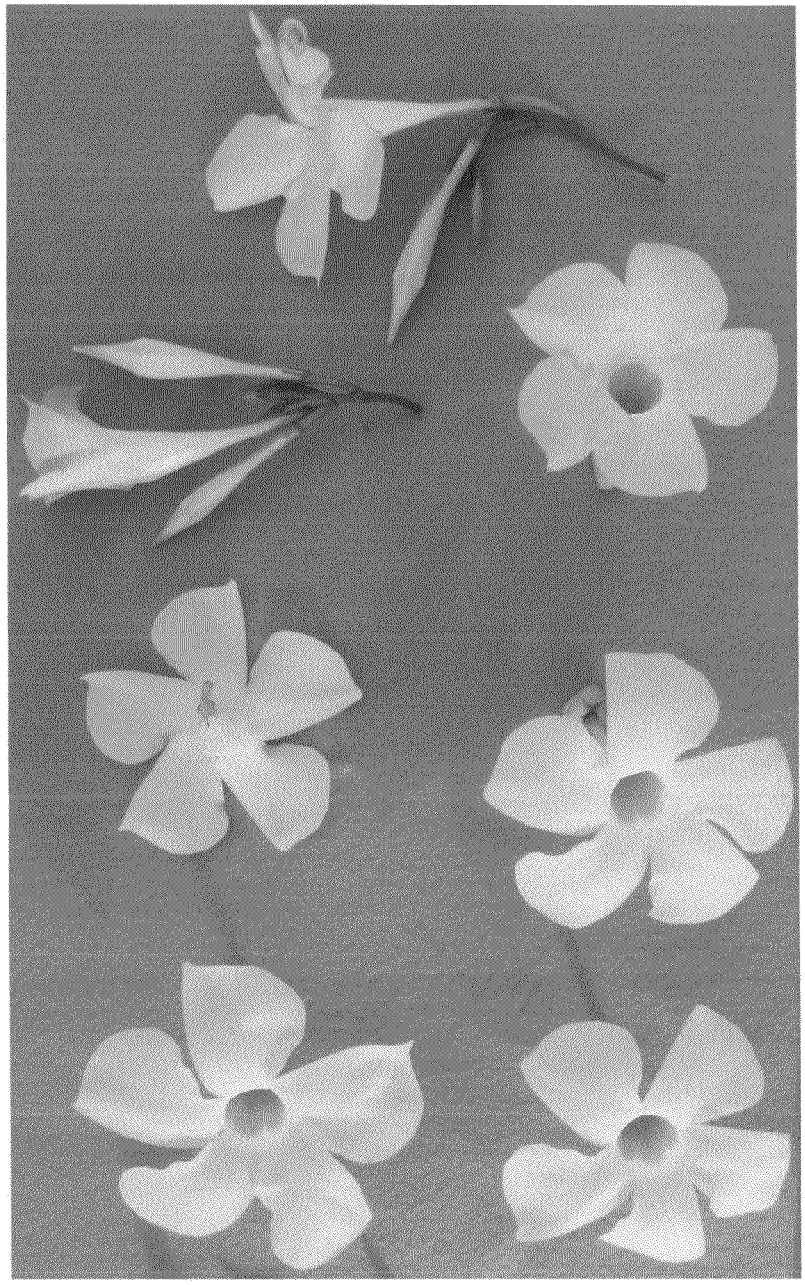

* * * * *